US010105119B2

(12) United States Patent
Marcelis et al.

(10) Patent No.: US 10,105,119 B2
(45) Date of Patent: Oct. 23, 2018

(54) PHANTOM AND METHOD FOR QUALITY ASSURANCE OF A PARTICLE THERAPY APPARATUS

(71) Applicant: Ion Beam Applications S.A., Louvain-la-Neuve (BE)

(72) Inventors: Simon Marcelis, Brussels (BE); Yves Claereboudt, Nil-Saint-Vincent (BE); Thierry Mertens, Nuremberg (DE); Frédéric Dessy, Binche (BE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 0 days.

(21) Appl. No.: 15/567,879

(22) PCT Filed: Apr. 22, 2016

(86) PCT No.: PCT/EP2016/059009
§ 371 (c)(1),
(2) Date: Oct. 19, 2017

(87) PCT Pub. No.: WO2016/170115
PCT Pub. Date: Oct. 27, 2016

(65) Prior Publication Data
US 2018/0098745 A1  Apr. 12, 2018

(30) Foreign Application Priority Data

Apr. 24, 2015 (EP) ..................... 15165139

(51) Int. Cl.
*G01D 18/00* (2006.01)
*A61B 6/00* (2006.01)
(Continued)

(52) U.S. Cl.
CPC ................ *A61B 6/584* (2013.01); *A61B 6/12* (2013.01); *A61B 6/4014* (2013.01);
(Continued)

(58) Field of Classification Search
CPC ................ A61N 5/1048; A61N 5/1075; A61N 2005/1076; A61N 2005/1087; A61B 6/583

See application file for complete search history.

(56) References Cited

U.S. PATENT DOCUMENTS 7,356,120 B2 * 4/2008 Main .................... A61N 5/1048
250/252.1
9,192,787 B2 * 11/2015 Dessy .................. A61N 5/1075
(Continued)

FOREIGN PATENT DOCUMENTS

DE  202011104321 U1  11/2011
EP  0514971 A1  11/1992
(Continued)

OTHER PUBLICATIONS

International Search Report for International Application No. PCT/EP2016/059009 from the European Patent Office, dated Jun. 17, 2016.
(Continued)

*Primary Examiner* — Kiho Kim
(74) *Attorney, Agent, or Firm* — Finnegan, Henderson, Farabow, Garrett & Dunner LLP

(57) ABSTRACT

A phantom and method for quality assurance of a particle therapy apparatus used in the intensity modulated particle therapy (IMPT) mode is provided. The phantom comprises a frame structure having a first face and a second face that is parallel to the first face. The phantom further comprises one or more wedges, and a first and second block of material each having a first block face and a second block face parallel thereto. In addition, the phantom further includes an absolute dosimeter arranged at the first block face. A plu-
(Continued)

rality of beads of high density material is located in the first or second block, and a 2D detector is arranged at the second face of the frame structure.

20 Claims, 6 Drawing Sheets

(51) Int. Cl.
    *A61B 6/12* (2006.01)
    *A61N 5/10* (2006.01)
(52) U.S. Cl.
    CPC ......... *A61N 5/1044* (2013.01); *A61N 5/1071* (2013.01); *A61N 5/1075* (2013.01); *A61N 2005/105* (2013.01); *A61N 2005/1061* (2013.01); *A61N 2005/1076* (2013.01); *A61N 2005/1087* (2013.01)

(56) References Cited

U.S. PATENT DOCUMENTS

2008/0217561 A1* 9/2008 Mackie ................ A61N 5/1048
                                                       250/492.3
2008/0219410 A1    9/2008 Gunzert-Marx et al.
2015/0085993 A1    3/2015 Scheib et al.

FOREIGN PATENT DOCUMENTS

EP          2422847 A1   2/2012
WO    WO 2013/160379 A1  10/2013

OTHER PUBLICATIONS

Written Opinion of the International Searching Authority for International Application No. PCT/EP2016/059009 from the European Patent Office.

* cited by examiner

PHANTOM AND METHOD FOR QUALITY ASSURANCE OF A PARTICLE THERAPY APPARATUS

CROSS-REFERENCE TO RELATED PATENT APPLICATIONS

This application is a U.S. national stage entry under 35 U.S.C. § 371 of International Application No. PCT/EP2016/059009, filed Apr. 22, 2016, which claims the benefit of European Patent Application No. 15165139.5, filed Apr. 24, 2015, all of which are hereby incorporated by reference in their entirety.

FIELD OF THE INVENTION

The invention is related to the field of particle therapy. More particularly, the invention is related to a phantom and method for quality assurance of a particle therapy apparatus used in the intensity modulated particle therapy (IMPT) mode also known as pencil beam scanning technique.

DESCRIPTION OF PRIOR ART

In current proton beam facilities, the Pencil Beam Scanning technique (PBS) involves the irradiation of separate spots in a target, each spot having a predefined position and depth, with a pre-defined dose being prescribed for each spot. In each treatment room of the facility, various characteristics of the delivered beam are subjected to a daily verification routine. These characteristics are:
 beam range: the position of the Bragg peak at a given beam energy in a given target, usually a water phantom or multi-layer ionization chamber,
 spot position and spot size, measured by a suitable 2D-detector, for example an array of ionization chambers or a scintillator screen equipped with a CCD camera,
 the deposited dose, measured by an absolute ionization chamber, for checking the output factor of the irradiation installation.

Each of these characteristics are commonly measured at a number of distinct beam energy levels, by a separate measurement device. A complete verification involves many manual operation, including entrance in the treatment room for adapting a phantom or a measuring device. Therefore, the time needed to complete a verification routine is therefore in the order of 30 to 60 minutes. Such long verification times are reducing the efficiency of the treatment facility in terms of the number of treatments that can be performed per day.

Document EP2422847 is related to a dosimetry device for verification of a radiation beam in standard and conformal radiation (i.e. high energy X-rays and not particles) therapy, and in particular in IMRT (Intensity Modulated Radiation Therapy). The device comprises an active area comprising lines of radiation detectors, and a build-up plate provided with degraders of different thicknesses. This device is designed with the specific aim of verifying the functioning of a multi-leaf collimator typically used in a radiation therapy apparatus, but not for performing a global verification of a particle therapy apparatus. This device is not suitable for measuring a beam range of a particle beam, because the thickness of the build-up plate is not adapted to the position of a Bragg peak produced by a hadron beam of a predefined energy.

Document WO2013160379 discloses an apparatus and method for hadron beam verification, allowing to verify characteristics of the beam emitted by a particle therapy apparatus, including range, spot size and spot position. However, this apparatus and method is not designed for performing a global verification of a particle therapy apparatus, including components such as a patient positioning system, an RX-ray imaging system. No means are provided for allowing to determine the correct alignment of the particle beam vs. the X-ray source(s), nor of the patient positioning system.

SUMMARY OF THE INVENTION

It is an object of the present invention to provide a phantom and method for quality assurance of a particle therapy apparatus used in the intensity modulated particle therapy (IMPT) mode, allowing to perform a fast and reliable verification of the particle therapy apparatus. More precisely, there is a need for a phantom allowing performing an alignment of a beam of particles emitted by the particle therapy apparatus in relation to two or more X-ray systems each comprising an X-ray source and a 2D X-xay detector.

The invention is defined by the independent claims. The dependent claims define advantageous embodiments.

According to a first aspect of the invention there is provided a phantom for quality assurance of a particle therapy apparatus usable in the intensity modulated particle therapy (IMPT) mode comprising (a) a frame structure having edges made of an RX-transparent material, having a first face and a second face parallel to said first face; (b) one or more wedges each having a first wedge face oriented to said first face and parallel thereto and a second wedge face oriented opposite to said first face and inclined with respect to said first face; (c) a first block of material having a first block face oriented to said first face and parallel thereto, and a second block face oriented to said second face and parallel thereto, an absolute dosimeter being arranged at said first block face; (d) a second block of material having a first block face oriented to said first face and parallel thereto, and a second block face oriented to said second face and parallel thereto; (e) a plurality of beads of high density material being located in said first and/or said second block; (f) a 2D detector arranged at said second face. According to the invention said one or more wedges, first block of material, absolute dosimeter, second block of material, plurality of beads of high density material and 2D detector are in a known fixed position in relation to said frame structure. The phantom of the invention may comprise a central bead of high density material maintained in a central known fixed position in relation to the frame structure, said one or more wedges, said first and second block of material being arranged in said frame structure so that a beam traversing said phantom from said from said first surface and perpendicularly thereto, through said central bead, will attain said second surface without traversing any material besides said central bead.

Preferably, the frame structure is in the shape of a polyhedron, more preferably is a rectangular cuboid.

Visual markers may be provided at a known position of one or more of said edges.

Preferably, the one or more wedges comprise parts having a distance between said first face and second face comprised between 20 mm and 315 mm and are made of a material having water-equivalent radiation absorbing properties. By selecting such distances, a Bragg peak of a particle beam emitted by said particle therapy apparatus and penetrating said first wedge face will occur at said second wedge face, for beam energies in the range of energies commonly used for particle therapy.

Preferably, the wedges and/or the first block and/or the second block are made of a material having water-equivalent radiation absorbing properties. A material having water-equivalent radiation absorbing properties is a material wherein a particle beam loses the same amount of energy during its travel through the material, as it would lose in the same penetration distance in water.

Preferably, the 2D detector is maintained to the edges of said second face by means of clips.

Preferably, the plurality of high density material beads are metallic spheres having a diameter between 1 and 3 mm.

According to a second aspect of the invention there is provided a method for quality assurance of a particle therapy apparatus usable in the intensity modulated particle therapy (IMPT) mode, said apparatus comprising a patient positioner having a reference position and two or more X-ray systems each comprising an X-ray source and a 2D X-ray detector, comprising the steps of:
 a) providing a phantom according to the invention;
 b) positioning said phantom on said patient positioner;
 c) positioning said patient positioner at said reference position;
 d) irradiating said phantom with a pencil beam directed at said central known fixed position of said phantom, and acquiring an image of said pencil beams on said 2D detector;
 e) from said image, computing the distance between the central bead and said pencil beam.

Preferably, the method may further comprise between the steps b) and c) the steps of
 f) positioning said patient positioner at a known offset vector from said reference position;
 g) acquiring one or more X-ray images of said phantom on said 2D X-ray detector;
 h) from the images of said high density material beads on said 2D X-ray detector, computing a correction vector for moving said patient positioner to said reference position;
 i) verifying that said the sum of said offset vector and of said correction vector is less than a threshold;

More preferably, the method may further comprise further comprising after step c) the steps of
 j) irradiating said phantom (10) for a plurality of pencil beams each having same energy, and acquiring the images of said pencil beams on said 2D detector (180);
 k) from said images, computing the beam range, spot size, spot position;
 l) acquiring the radiation dose from said absolute radiation detector (130);
 m) verifying that said beam range, spot size, spot position and radiation dose are within a range from expected beam range, spot size, spot positions and radiation dose.

Alternatively, there is provided a method for quality assurance of a particle therapy apparatus used in the intensity modulated particle therapy (IMPT) mode, said apparatus comprising a patient positioner having a reference position and two or more X-ray systems each comprising an X-ray source and a 2D X-ray detector, comprising the steps of:
 n) providing a phantom according to the invention;
 o) positioning said phantom on said patient positioner;
 p) positioning said patient positioner at a known offset vector from said reference position;
 q) acquiring one or more X-ray images of said phantom on said 2D X-ray detector;
 r) from the images of said fiducials on said 2D X-ray detector, computing a correction vector for moving said patient positioner to said reference position;
 s) verifying that said the sum of said offset vector and of said correction vector is less than a threshold;
 t) positioning said patient positioner at said reference position;
 u) irradiating said phantom for a plurality of pencil beams each having same energy, and acquiring the images of said pencil beams on said 2D detector;
 v) from said images, computing the beam range, spot size, spot position;
 w) acquiring the radiation dose from said absolute radiation detector;
 x) verifying that said beam range, spot size, spot position and radiation dose are within a range from expected beam range, spot size, spot positions and radiation dose.

According to a preferred method, when said phantom comprises visual markers at a known position of one or more of the frame edges further the method may comprises comprising the steps of
 a) directing one or more fans of light or laser light to said visual markers;
 b) verifying the coincidence of said fans of light or laser light with said visual markers.

The steps j) to m) may be repeated for different beam energies.

Advantageously, at least one of steps c) to m) are performed automatically under control of a program.

According to a third aspect of the invention there is provided a computer program comprising code for performing at least some of steps c) to m) of the methods of the invention.

According to a fourth aspect of the invention there is provided a system comprising a phantom according to the invention and a controller comprising a computer program according to the invention, for the quality assurance of a particle therapy apparatus.

According to a fifth and last aspect of the invention there is provided a phantom for quality assurance of a particle therapy apparatus comprising
 a) a 2d detector for detecting particles, having an xy detector plane;
 b) a wedge-shaped block having a surface parallel with said xy detector plane and a surface inclined with respect to said xy detector plane;
 c) 2 or more imaging markers located on a first supporting block
 d) a second block configured for supporting a dosimeter detector wherein the phantom further comprises a reference marker positioned along a line essentially perpendicular to said xy detector plane and wherein the wedge-shaped block, first block and second block are located and configured for not intercepting said line.

SHORT DESCRIPTION OF THE DRAWINGS

These and further aspects of the invention will be explained in greater detail by way of example and with reference to the accompanying drawings in which.

The drawings of the figures are neither drawn to scale nor proportioned. Generally, identical components are denoted by the same reference numerals in the figures.

DETAILED DESCRIPTION OF EMBODIMENTS OF THE INVENTION

Figure 1:
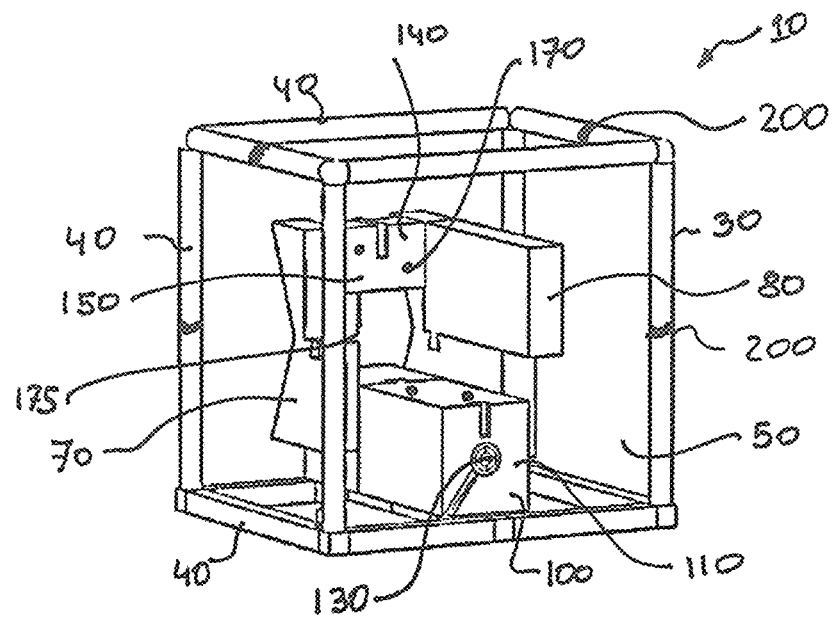
FIG. 1 is a perspective view of a phantom according to an embodiment of the invention.

FIG. 1 is a perspective view of a phantom 10 according to an embodiment of the invention. A frame structure 30 comprises a set of edges 40 and forms a polyhedron, which, in the example shown, is a rectangular cuboid. A first face of said cuboid may be used a beam entry face, i.e. this face is oriented towards the beam source when the phantom is in use. These edges are made of an X-ray transparent material, e.g. carbon fibre, and assembled without metallic pieces, e.g. by gluing. The phantom 10 comprises a series of wedges 70 that will be described later. The phantom comprises a first block of material 100 having a first face 110, and a second face 120, which are parallel respectively, to the first 50 and second 60 faces of the frame structure 30. An absolute dosimeter 130 is located and the first face 110 of this first block, and may be used for measuring the dose emitted by the beam source. An ionization chamber may be used as an absolute dosimeter. Between the first block of material 110, and a second block of material 140, an open channel is provided allowing a beam entering the phantom 10 through the first face 50, and perpendicular thereto, to go through the frame structure without traversing any material, except for a central high density material bead located along a central line of this channel, conveniently located on a line passing through the centres of the first 50 and second 60) faces of the frame structure 30. This central bead 175 may conveniently be maintained in this position through a rod of X-ray transparent material attached to one of the components of the phantom 10, e.g. as shown of FIG. 1, on to the second block 140. In addition to the central bead 175, a set of additional beads 170 are located at known positions in the phantom. In the example shown, two beads 170 are located on the first face 150 of the second block 140, and two beads 170 are located on the upper face of the first block 100. The function and role of these beads 170, 175 will be explained in relation to the method of the invention. By "high density material" it is meant a material having a density higher than 1 so that the beads are visible under X-ray imaging and on the 2D detector under particle beam. Beads made of metal e.g. steel are convenient for this purpose. The use of spheres in the range of 1 to 3 mm, e.g. 2 mm was found convenient for providing sufficient visibility in the images and a good precision in positioning. The beads may be fixed in holes drilled in the blocks of material. Visual markers 200 may be provided at known positions on the edges 40 of the frame structure 30. The function and use of these visual markers 200 will be discussed below.

Figure 2:
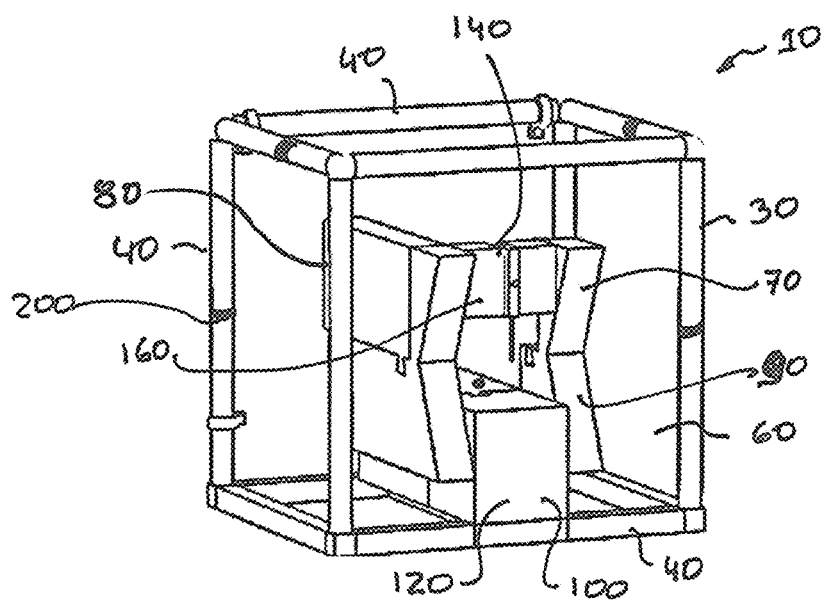
FIG. 2 is a perspective view of same phantom seen from the other side.

FIG. 2 is a perspective view of same phantom seen from the other side, showing same components. In the example shown, four wedges are provided and the second wedge faces 90 are inclined at an angle of 24° with respect to the second face 60 of the frame structure 30. The second face 120 of the first block 100 and the second face 160 of the second block appear.

Figure 3:
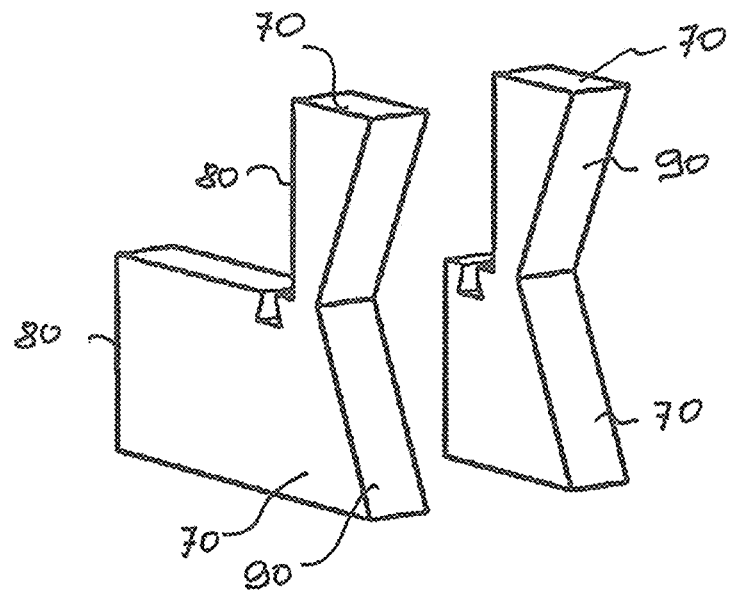
FIG. 3 is a perspective view of the wedges of same.

FIG. 3 is a perspective view of the wedges of the phantom of FIG. 2. The two upper wedges have a beam path length of 65 mm at the upper part and 20 mm at the bottom part, and a path length of 42.5 mm at mid-height. When the wedges are made of water-equivalent material, this corresponds to the depth of the Bragg peak of a beam of protons having an energy of 73.37 MeV. Similarly, the bottom right wedge is dimensioned for having a path length at mid-height of 82.5 mm corresponding to a 106.4 MeV energy, and bottom left wedge is dimensioned for having a path length at mid-height of 192.5 mm corresponding to a 172.53 MeV energy Bragg peak. Additional blocks having e.g. lengths of 70 mm, 100 mm, 200 mm and 250 mm, may be appended to the upper wedges (through the dovetail assembly shown) for reaching path length at mid height of 142.25 mm, 242.50 and 292.50 mm, corresponding to the depths of Bragg peaks of 145.13 MeV, 197.22 MeV, 220.9 MeV, respectively. As is known in the art, a particle therapy apparatus is designed for treating tumours located in the body of a patient, at some range of depth. Therefore, the apparatus is designed for being able to produce particle beam having an energy range producing Bragg peak depths corresponding to said range of depths. The man skilled in the art will know how to select the dimensions of the one or more wedges for measuring the beam energy in the range needed for the particle therapy apparatus to be verified.

Figure 4:
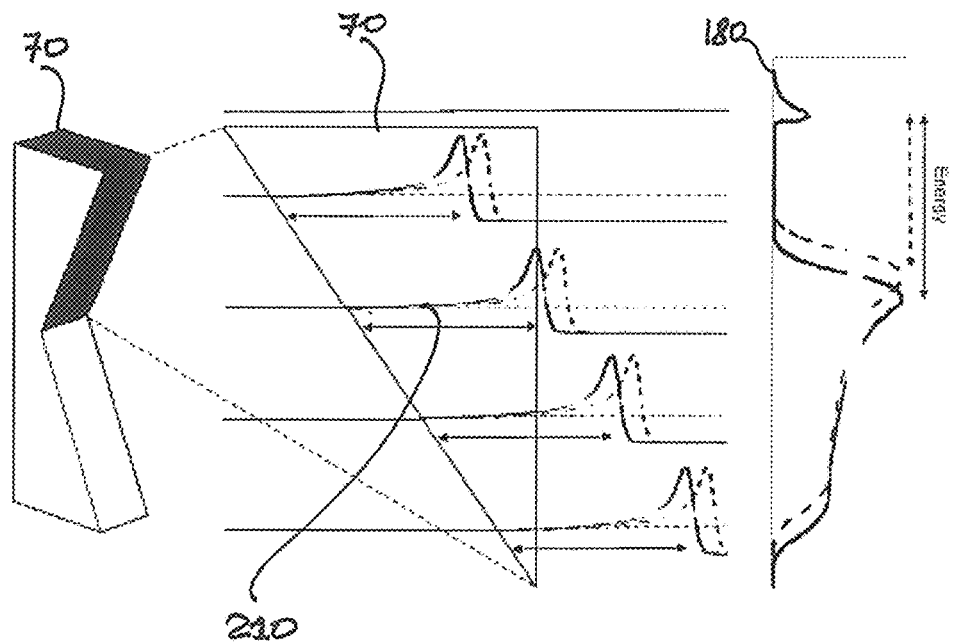
FIG. 4 is a schematic view of a beam traversing a wedge and corresponding image.

FIG. 4 illustrates how the beam energy is determined using the phantom and method of the invention. A beam (or a set of individual pencil beams) are directed towards the first face 80 of the wedge or wedges. The dose deposited in the 2D detector after the beam passed through the wedge is measured. The height at which the detected dose is maximal corresponds to the Bragg peak, and the corresponding path length 210 in the wedge gives the Bragg peak depth, which corresponds in a known manner to the beam energy.

Figure 6A:
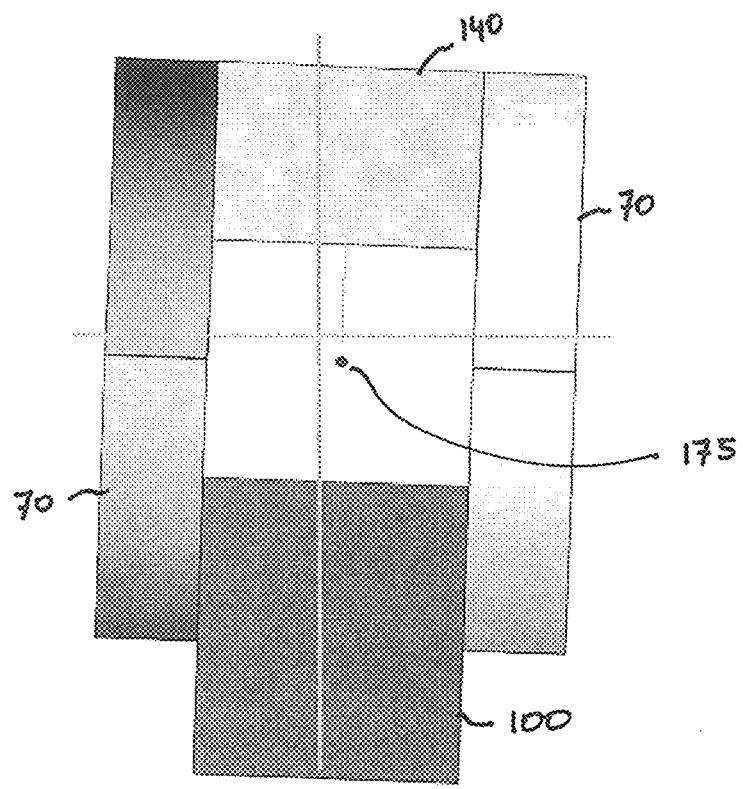
FIGS. 6a and 6b are a schematic view of the phantom at a known offset position and at the reference position, respectively.
Figure 6B:
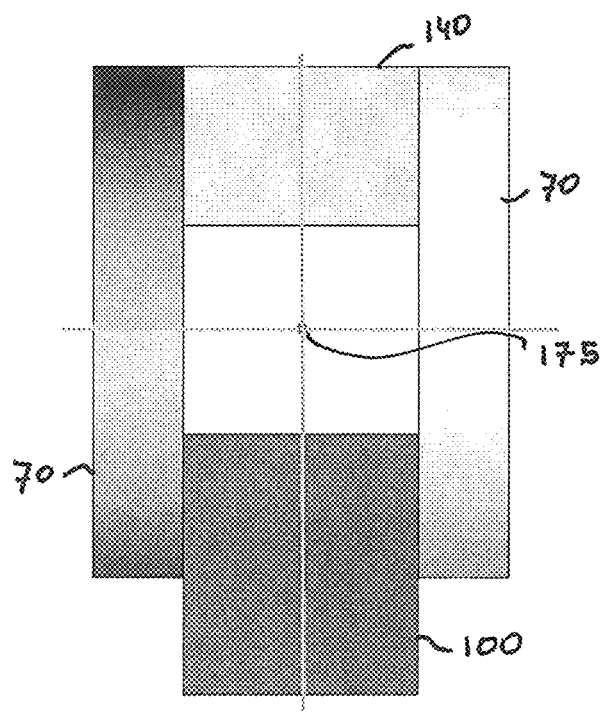

Using the phantom of the invention, it is possible to efficiently and rapidly verify the functioning of components of the radiation therapy apparatus, including the X-ray imaging sources and detectors, positioning system, and the control system used for managing these components. The phantom is positioned at a nominal position on the patient positioner (the patient table). The patient positioner is positioned at a known offset position from a reference position. This offset position may include space translation (x, y, z) as well as angular direction and orientation. The X-ray imaging system is then used to take shots of the phantom, and from the images of the beads 170, 175 on the X-ray detectors, a correction vector may be computed in a known manner. The addition of the offset and correction (translational as well as rotational) should be zero and any deviance from zero should be treated as a potential default in the system. All these steps may advantageously be performed under program control. The acquired X-ray images may be processed by a program in order to compute the correction vector. The patient positioner is then moved to the reference position. This reference position may be a position such that the 2D detector is positioned at the isocenter of the particle therapy apparatus. At this stage, and additional check maybe performed for verifying that the phantom is at a correct position: A set of (laser) light sources are installed at fixed and known positions around the reference position and direct fan beams of (laser) light. The sources are installed and directed in order to reach the visual markers 200 on the edges of the frame structure 30. The image of these fan beams on these markers 200 is observed in order to ascertain that the phantom is in the right position. Again these steps, including the acquisition and processing of the images may advantageously be performed automatically under program control. FIGS. 6a and 6b are schematic views of the phantom at the known offset position and at the reference position, respectively.

Figure 5:
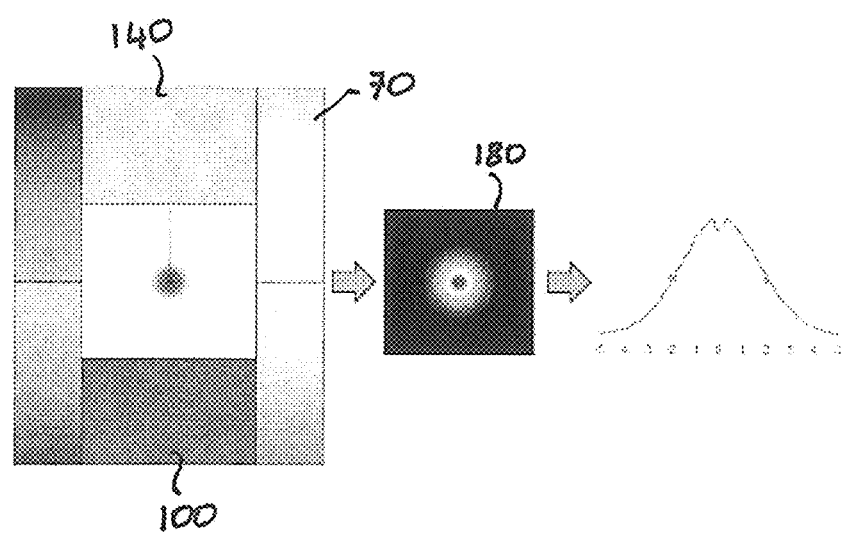
FIG. 5 is a schematic view of the central bead of same phantom, and corresponding image.

The function of the central bead 175 will now be discussed. When the phantom has been positioned at the reference position, a beam of particles is directed at the phantom along the central line. The corresponding image acquired from the 2D detector is shown in the middle of FIG. 5, and a corresponding histogram is shown on the right hand part of FIG. 5. The peak corresponds to the beam, and the centroid of this peak can be determined e.g. by taking the mid-point between two points located at mid-height of the peak. The valley at the top of the peak is resulting from the absorption produced by bead 175. The centre of this valley corresponds to the bead position. This histogram allows the verification of the alignment of the beam with respect to the geometric alignment performed with the X-ray system. The centroid of the peak of the beam should coincide with the centre of the valley at the top of the peak, caused by the central bead 175. The steps of controlling the directions of the central beam, acquisition of the 2D detector, and processing of the image for providing a verification signal may be performed automatically under program control.

Figure 7A:
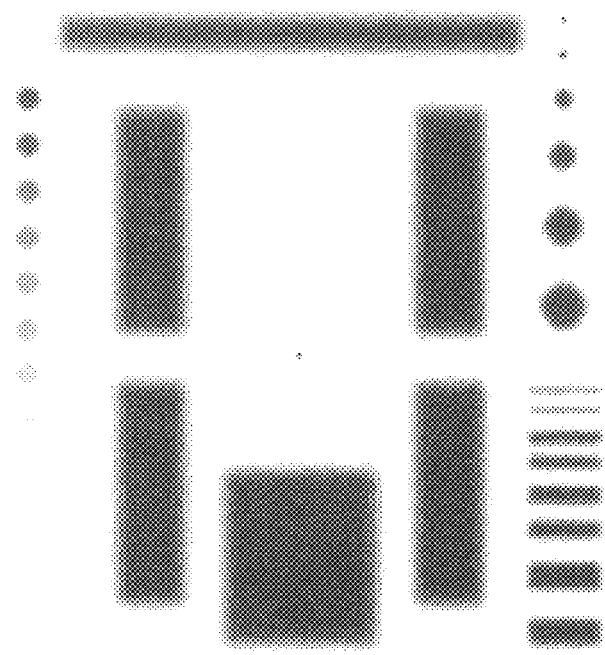
FIGS. 7a and 7b are a schematic view of a plurality of pencil beam irradiated, and corresponding images, respectively.
Figure 7B:
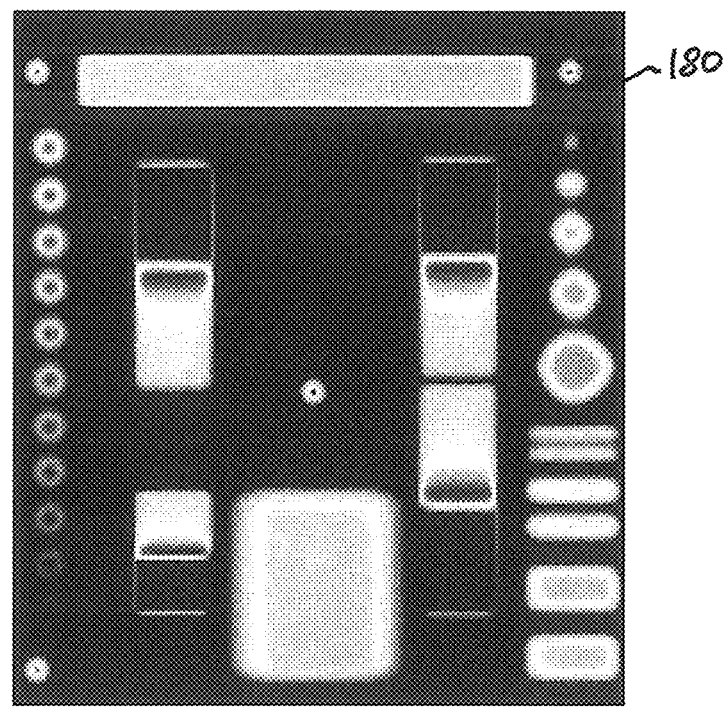

FIG. 7a represents the sequence of beams that are produced under program control by the radiation therapy apparatus, and directed to the phantom in reference position. FIG. 7b represents the corresponding image acquired from the 2D detector. From these images, different parameters may be obtained such as the beam energy and alignment, as discussed above. Also spot size and position may be verified in a known manner.

Figure 8:
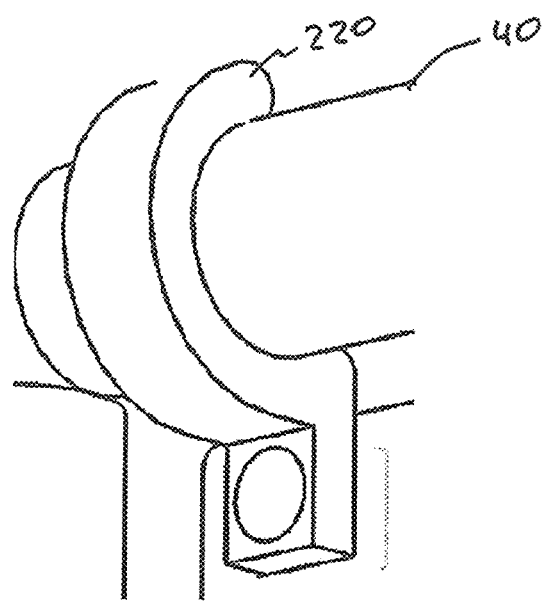
FIG. 8 Is a detailed view of means for fastening a film to the frame structure.

The presence of a frame structure 30 in the phantom 10 of the invention has many advantages: the phantom may be manipulated easily, the frame is a reliable and precise reference for position of the various components of the phantom, the markers 200 allow a precise position verification with laser lights. In addition, the edges 40 may be used for affixing components to the frame: the 2D detector may be a film detector maintained to the frame through plastic clips 220 as shown on FIG. 8. The 2D detector may also be a scintillator-base detector with a camera and be attached to the frame through clips 220.

By using the phantom and method of the invention, it is possible to perform a daily verification of the functioning of a particle therapy apparatus, including components of said apparatus such as the positioning system, X-ray imaging system, beam directing system, dose, in a reliable way. When performed under program control, the method is particularly efficient and fast, allowing to perform a full quality assurance in less than 10 minutes. With the method of the invention, the therapists saves many time consuming operations such as entering the treatment room for performing a change to a phantom, and exiting the treatment room for performing the measurements.

The present invention has been described in terms of specific embodiments, which are illustrative of the invention and not to be construed as limiting. More generally, it will be appreciated by persons skilled in the art that the present invention is not limited by what has been particularly shown and/or described hereinabove.

Reference numerals in the claims do not limit their protective scope. Use of the verbs "to comprise", "to include", "to be composed of", or any other variant, as well as their respective conjugations, does not exclude the presence of elements other than those stated. Use of the article "a", "an" or "the" preceding an element does not exclude the presence of a plurality of such elements.

The invention claimed is:

1. A phantom for quality assurance of a particle therapy apparatus usable in the intensity modulated particle therapy (IMPT) mode, the phantom comprising:
   a) a frame structure, further comprising edges made of an RX-transparent material, a first face, and a second face parallel to the first face;
   b) one or more wedges, wherein each wedge further comprises a first wedge face oriented towards the first face and parallel to the first face and a second wedge face oriented opposite to the first face and inclined with respect to the first face;
   c) a first block of material having a first block face oriented towards the first face and parallel to the first face, a second block face oriented towards the second face and parallel to the second face, and an absolute dosimeter arranged on the first block face;
   d) a second block of material having a first block face oriented towards the first face and parallel to the first face, and a second block face oriented towards the second face and parallel to the second face;
   e) a plurality of beads of high density material located in the first block or the second block;
   f) a 2D detector arranged at the second face, wherein the one or more wedges, first block of material, absolute dosimeter, second block of material, plurality of beads of high density material, and 2D detector are fixed in position with respect to the frame structure; and
   g) a central bead of high density material fixed in a central position relative to the frame structure, wherein the one or more wedges, the first block, and the second block are arranged in the frame structure so that a beam traversing the phantom in a direction perpendicular to the first face and through the central bead will reach the second face without traversing any material besides the central bead.

2. The phantom of claim 1, wherein the frame structure is in the shape of a polyhedron.

3. The phantom of claim 2, wherein the polyhedron is a rectangular cuboid.

4. The phantom of claim 1, further comprising visual markers positioned on the edges.

5. The phantom of claim 1, wherein the one or more wedges further comprises a part between the first wedge face and the second wedge face, the part having a path length between 20 mm and 315 mm and comprising a material with water-equivalent radiation absorbing properties.

6. The phantom of claim 1, wherein at least one of the one or more wedges, the first block, or the second block is made of a material with water-equivalent radiation absorbing properties.

7. The phantom of claim 1, wherein the 2D detector is fixed to the edges of the second face by clips.

8. The phantom of claim 1, wherein the plurality of high density material beads further comprises metallic spheres of a diameter between 1 and 3 mm.

9. A method for quality assurance of a particle therapy apparatus usable in the intensity modulated particle therapy (IMPT) mode, the apparatus comprising a patient positioner having a reference position and two or more X-ray systems each comprising an X-ray source and a 2D X-ray detector, the method comprising:
- a) providing a phantom of claim 1;
- b) positioning the phantom on the patient positioner;
- c) positioning the patient positioner at the reference position;
- d) irradiating the phantom with a pencil beam directed at a central position of the phantom, and acquiring an image of the pencil beam on the 2D X-ray detector;
- e) from the image, computing a distance between the central bead and the pencil beam.

10. The method of claim 9, further comprising between steps b) and c):
- f) positioning the patient positioner at a known offset vector from the reference position;
- g) acquiring one or more X-ray images of the phantom on the 2D X-ray detector;
- h) from the images of the high density material beads on the 2D X-ray detector, computing a correction vector for moving the patient positioner to the reference position; and
- i) verifying that a sum of the offset vector and the correction vector is less than a threshold.

11. The method of claim 9, further comprising after step c):
- j) irradiating the phantom for a plurality of pencil beams each having same energy, and acquiring images of the pencil beams on the 2D X-ray detector;
- k) from the images, computing a beam range, spot size, and spot position;
- l) acquiring a radiation dose from an absolute radiation detector;
- m) verifying that the beam range, spot size, spot position and radiation dose are within expected ranges of beam range, spot size, spot position and radiation dose.

12. The method of claim 9, wherein the phantom comprises visual markers positioned on one or more edges, the method further comprising:
- n) directing one or more fans of light or laser light to the visual markers;
- o) verifying coincidence of the fans of light or laser light with the visual markers.

13. The method of claim 9, further comprising repeating steps j) to m) for different beam energies.

14. The method of claim 9, wherein at least one of steps c) to m) are performed automatically under control of a program.

15. The method of claim 9, further comprising:
acquiring a histogram that corresponds to the image; and
verifying that the phantom has been positioned at the reference position based on a valley on the histogram caused by the central bead on a histogram.

16. The phantom of claim 1, further comprising a rod of X-ray transparent material attached to a portion of the phantom,
wherein the rod is configured to fix the central bead in the central position relative to the frame structure.

17. The phantom of claim 1, wherein:
an upper portion of the one or more wedges has a path length of 65 mm and further comprises a material with water-equivalent radiation absorbing properties, and
a bottom portion of the one or more wedges has a path length of 20 mm and further comprises a material with water-equivalent radiation absorbing properties.

18. The phantom of claim 1, wherein the high density material further comprises metal.

19. The phantom of claim 1, wherein:
the first block or the second block further comprises a plurality of drilled holes, and
the plurality of high density material beads are fixed to the drilled holes.

20. A phantom for quality assurance of a particle therapy apparatus, the phantom comprising:
- a) a 2D detector for detecting particles, the detector having an x-y detector plane;
- b) a wedge-shaped block having a first surface parallel to the x-y detector plane and a second surface inclined with respect to the x-y detector plane;
- c) two or more imaging markers located on a first supporting block;
- d) a second block configured to support a dosimeter detector,
wherein the phantom further comprises a reference marker positioned along a line essentially perpendicular to the x-y detector plane, and wherein the wedge-shaped block, the first block, and the second block do not intercept the line.

* * * * *